United States Patent [19]

Tokoro

[11] Patent Number: 5,080,895
[45] Date of Patent: Jan. 14, 1992

[54] SPECIFIC ANTIBODY-CONTAINING SUBSTANCE FROM EGGS AND METHOD OF PRODUCTION AND USE THEREOF

[75] Inventor: Hideo Tokoro, Tokyo, Japan

[73] Assignee: Ghen Corporation, Gifu, Japan

[21] Appl. No.: 679,839

[22] Filed: Apr. 1, 1991

Related U.S. Application Data

[63] Continuation of Ser. No. 338,417, Aug. 4, 1988, abandoned, which is a continuation of Ser. No. 933,187, Nov. 21, 1986, abandoned.

[30] Foreign Application Priority Data

Nov. 25, 1985 [JP] Japan .................. 60-264108
Sep. 17, 1986 [JP] Japan .................. 61-218859

[51] Int. Cl.$^5$ .................... A61K 39/395
[52] U.S. Cl. .................... 424/85.8; 424/88; 530/367; 530/368; 530/387
[58] Field of Search .............. 424/85.8, 88; 530/387

[56] References Cited

U.S. PATENT DOCUMENTS

| | | |
|---|---|---|
| 3,984,539 | 10/1976 | Khouw et al. .............. 424/85 X |
| 4,284,623 | 8/1981 | Beck .............. 424/85 |
| 4,340,591 | 7/1982 | Luccotte et al. .............. 530/368 X |
| 4,357,272 | 11/1982 | Polson .............. 530/387 |
| 4,402,938 | 9/1983 | Collins et al. .............. 424/85 |
| 4,534,971 | 8/1985 | Fisher .............. 514/21 |
| 4,550,019 | 10/1985 | Polson .............. 424/85 |

FOREIGN PATENT DOCUMENTS 0152270 8/1985 European Pat. Off.
2057451A 4/1981 United Kingdom.

OTHER PUBLICATIONS

"Antibodies to Human Plasma Kallikrein from Egg Yolks of an Immunized Hen: Preparation and Characterization", D. Burger et al., *Chemical Abstracts*, vol. 104, No. 1 (1986), p. 410, Abstract 4457t.

"Antibodies to Calf Thymus RNA Polymerase II from Egg Yolks of Immunized Hens", Sean B. Carroll et al., *Chemical Abstracts*, vol. 98, No. 9 (1983), p. 468, Abstract 70128y.

"Isolation of Viral IgY Antibodies from Yolks of Immunized Hens", A. Polson et al., *Chemical Abstracts*, vol. 94, No. 5 (1981), p. 400, Abstract 28656h.

"Antibodies to Proteins from Yolk of Immunized Hens", A. Polson et al., *Chemical Abstracts*, vol. 94, No. 5 (1981), p. 405, Abstract 28708b.

"Lack of Antigen Fragments in Guinea Pig Transfer Factor-Like Activity", W. Dunnick et al., *Biological Abstracts*, vol. 71, No. 1 (1981), p. 302, Ref. 2892.

Stedman's Medical Dictionary, 1987, p. 494.

Primary Examiner—Howard E. Schain
Attorney, Agent, or Firm—Burns, Doane, Swecker & Mathis

[57] ABSTRACT

A substance which contains a specific antibody or specific transfer factor-like component is produced from the yolks or albumens or both of eggs of a hen which has been immunized against a selected antigen such as a pathogenic bacteria. The substance is active against the antigen, and is useful for protecting animals from attack by the same antigen as used in immunization of the hen. It is also useful as additives in food for animals, cosmetics, and medicines. The transfer factor-like component is recovered from a fraction of at most 10,000 in molecular weight of the yolks or albumens or both of the eggs.

7 Claims, 3 Drawing Sheets

SPECIFIC ANTIBODY-CONTAINING SUBSTANCE FROM EGGS AND METHOD OF PRODUCTION AND USE THEREOF

This application is a continuation U.S. Ser. No. 07/338,417, filed Aug. 4, 1988 now abandoned, which in turn is a continuation of U.S. Ser. No. 06/933,187, filed Nov. 21, 1986 (now abandoned).

BACKGROUND OF THE INVENTION

1. Field of the Invention

This invention relates to a specific antibody-containing substance which is produced from an egg of a hen immunized against a selected antigen and which contains an antibody specific for the antigen, as well as a method of the production and use thereof. The present invention also relates to a substance which is produced from an egg of a hen immunized against a selected antigen and which contains a transfer factor-like component specific for the antigen, as well as a method of the production and use thereof.

2. Description of the Prior Art

U.S. Pat. No. 4,402,938 (Collins et al.) discloses a method which comprises introducing pre-partum an antigen into the udder of an ungulate, collecting the colostrum and milk produced following the colostrum, removing the fat and solids from the colostrum and milk so that only whey remains, and passing the whey through a filter having a pore size of about 0.2 microns in an ultrafiltration unit to yield as a filtrate a product which contains an unknown food factor having a molecular weight on the order of 1200 or less. According to the method, the antigen can be selected from pollen, bacteria, viruses, molds, allergens, blood from sick animals, sperm, and toxins. The product which contains the above food factor is useful as a nutrition supplement for animals.

However, according to the above method, the antigen must be administered to the ungulate during the last month of gestation, and it is critical to collect the colostrum which is produced for a very limited period, usually a few days, after parturition. Thus, the production of the above-mentioned food factor in a large amount necessitates a vast farm, and it is very difficult to use such a vast farm for constant practice of the above method in countries having limited land such as Japan or the U.K.

In addition, the method disclosed in the above U.S. Pat. involves very complicated procedures in that the colostrum and the subsequently-collected milk have to be treated separately and they must be frozen for a period as long as 60 days or more in order to precipitate and remove the solids.

The above U.S. Pat. also describes that the product obtained by the ultrafiltration with a filter having a pore size of about 0.2 microns may contain, in addition to the food factor, B lysin, conglutinin, interferon, lactoferrin, lactoperoxidase, B lymphocytes, T lymphocytes, lysozyme, macrophages, polypeptides, properdin, and thiocyanate, while proteins, globulins, and other large molecules having a molecular weight on the order of 1200 or more are removed from the product. These large molecules which are removed from the product and not used in the above method comprise beneficial active substances such as globulins, which contain an antibody specific for the antigen used in the immunization, and such specific antibody has a capability of protecting an animal when it is exposed to the same antigen.

It is well known in the art that when a specific antibody produced within the body of an animal by immunization against an antigen is administered to another animal, the animal to which the specific antibody is administered administered is effectively protected from attacks or infections by the same antigen as that used in the immunization since it is passively immunized against the antigen by the administration of the specific antibody which is active against the antigen. However, if the animal to which the antibody is administered and the immunized animal are not of the same species, repeated administrations of the antibody to the animal may cause anaphylactic shock due to a specific reaction with a heteroantibody formed in the body of the animal by the first administration. For this reason, such protection achieved by passive immunization with a heterogeneous antibody is generally applied for therapeutical purposes only to emergent situations, for example, the treatment of tetanus or snake bite.

Japanese Patent Laid-Open Application No. 60-248628 describes that a specific antibody or a specific antibody-containing fraction separated from an egg of a fowl or milk of a bovid which has been immunized against an antigen can be used for heterogeneous passive immunization of an animal against attacks by the same antigen as used in the immunization provided that the animal has acquired resistance to heterogeneous antibodies of the fowl or bovid by feeding the animal with a substance containing the heterogeneous antibodies such as milk or eggs for a long period in the range of 30 to 90 days. In Example 2 of that laid-open application, an ovular antibody-containing fraction was injected twice into rabbits which had not acquired resistance to the antibody. As a result, all the animals died due to anaphylactic shock.

Thus, the method of passive immunization disclosed in the above laid-open application requires a long period of at least 30 days before an animal is treated by the passive immunization using an ovular or bovine antibody. This means that it is very difficult to apply the method to actual treatment of infectious diseases. In addition, since the period required to acquire resistance to an antibody largely depends on the species, age, and health of the animal, the above method always involves the risk that it induces a serum sickness or even anaphylactic shock by a premature, repeated administration of the antibody.

There is no experimental data in the above Japanese laid-open application which demonstrate any therapeutical effect of administration of a specific antibody to an animal which has acquired resistance to the antibody. The only therapeutical experiment is shown in Example 3 of the laid-open application, in which an ovular antibody against *Streptococcus mutans* (Serotype C) was repeatedly administered per os. to germ-free rats which had not acquired resistance to ovular antibodies, and after 20 days the animals were challenged by bacteria of the same strain. The results were evaluated by the number of plaques found in molar teeth. However, there were no statistically significant differences between the results for the administered group and the control group. Furthermore, the experiment was conducted in germ-free rats which do not exist naturally by oral administration thereto of *S. mutans,* a bacterium which acts on cariogenesis in humans rather than rats. Therefore, the experiments do not provide reliable information on therapeutical effect which is attained by administration of the antibody or antibody-containing fraction disclosed in the laid-open application.

It is known that many infectious diseases in livestock and poultry such as pigs and fowls can be prevented by oral administration of an antibody against the bacterium which induces the disease. For this purpose, a number of methods of preparing or administering a substance which contains an antibody or antibody-like factor have been proposed in the art See, for example, the above-mentioned U.S. Pat. No. 4,402,938, and U.S. Pat. Nos. 3,984,539, and 4,284,623. However, most of the known methods use serum, colostrum, or milk from a cow to produce an antibody or antibody like factor. Therefore, these methods cannot be performed readily and conveniently in Japan or other countries having limited land, and the product thus produced is expensive.

In addition to prevention of infectious diseases in animals, a substance which contains a specific antibody or antibody-like factor has prospective usefulness as additives in foods for livestock and poultry, cosmetics, and medicines, and in the field of serodiagnosis Accordingly, it is desired to provide an antibody or antibody-like factor specific for a selected antigen or a substance containing such an antibody or antibody like factor which can be produced in large amounts and inexpensively.

SUMMARY OF THE INVENTION

It is an object of the present invention to provide a method for producing a substance which contains a specific antibody or transfer factor-like component as an active ingredient, the method being capable of producing such a substance inexpensively in large amounts at any season of the year.

It is another object of the present invention to provide an inexpensive substance which contains a specific antibody or transfer factor-like component as an active ingredient produced from an egg of a hen immunized against the selected antigen.

A further object of the present invention is to provide the use of such a substance which contains a specific antibody or transfer factor-like component as an active ingredient in the treatment of infectious or other diseases, and as additives in food for livestock and poultry, cosmetics, and medicines.

Other objects and advantages, as well as the nature of the present invention will be apparent from the following description.

In one aspect, the present invention provides a specific antibody-containing substance for oral applications obtained from the overall ovum or the yolk or albumen of an egg laid by a hen which has been immunized against a selected antigen. The substance contains an antibody specific for the antigen used in the immunization of the hen, and is active against the antigen. Thus, in accordance with the present invention, the desired antibody-containing substance is produced from an egg, and therefore it is possible to produce it inexpensively in large quantities at any season of the year. The specific antibody-containing substance may be the specific antibody per se (i.e., the immunoglobulin fraction) isolated from the overall ovum, yolk, or albumen of the egg in a conventional manner. In a preferred embodiment, however, the overall ovum, yolk, or albumen which contains the specific antibody may be stirred or homogenized into an emulsion and spray-dried to form a powder, which is recovered as the desired antibody-containing substance according to the present invention. The powder can be orally administered to animals affected by an intestinal infectious disease for therapeutical purposes.

In another aspect, the present invention provides a substance for oral and parenteral applications which contains a specific transfer factor-like component and which is obtained from a fraction of at most 10,000 molecular weight of the overall ovum or the yolk or albumen of an egg laid by a hen which has been immunized against a selected antigen. The transfer factor-like component contained in the substance is specific for the antigen used in the immunization and would have an activity for passive transfer of delayed-type hypersensitivity. Such substance contains no antibodies or immunoglobulins so that it can be applied parenterally. It is particularly useful in the treatment of various infectious diseases other than intestinal infectious diseases, as well as for use as additives in food for livestock and poultry, cosmetics, and medicines. The residual portion of the overall ovum, yolk, or albumen from which the fraction of at most 10,000 in molecular weight has been separated out to produce the above substance contains an antibody specific for the selected antigen, and can be utilized to produce the specific antibody-containing substance mentioned in the preceding paragraph.

DETAILED DESCRIPTION OF THE PREFERRED EMBODIMENTS

In order to produce the specific antibody-containing substance, or the specific transfer factor-like component-containing substance according to the present invention, a hen is immunized against a selected antigen. The antigen may be any substance to which the immune system of an animal will respond, and it can be selected according to the end use of the produced substance. The antigens which can be used in the present method include pollen, bacteria, viruses, molds, allergens, blood from affected animals, sperm, and toxins. A combination of two or more antigens or a polyvalent antigen may also be employed.

In the production of a substance which contains a specific antibody, it is preferable to select an antigen from pathogenic bacteria or factors which cause intestinal infectious diseases in animals. Since the antibody-containing substance according to the present invention can be applied to animals only by the oral route in order to avoid the risk of inducing a serum disease or anaphylactic shock, it is particularly beneficial to use such a substance in the treatment or prevention of intestinal infections. The pathogenic bacteria or factors which are particularly suitable for use in the production of an antibody-containing substance in the present invention include those coliform bacteria or factors which cause colibacillosis, particularly diarrhea such as "scour" in young animals such as piglets or calves. Specific examples of such bacteria or factors are porcine ETEC (enterotoxigenic *E. coli*) 987P, K88, and K99 antigens. Colibacillosis is a serious problem in livestock farming, since a new-born piglet or calf sometimes does not receive sufficient immunoglobulins from colostrum and therefore a considerable proportion of young piglets or calves suffer colibacillosis and scour, which are characterized by severe diarrhea and dehydration, and which frequently result in death.

In the production of a substance which contains a transfer factor-like component from a fraction of the yolk or albumen or both of an egg having a molecular weight of at most 10,000, the antigen used for this purpose can be selected from a wide variety of materials as listed above which act as an antigen in an animal, since such a substance is free of any antibody and can be applied parenterally with no risk of causing serum diseases and anaphylactic shock.

When the substance according to the present invention which contains a specific antibody or transfer factor-like component is used as an additive to food for animals, the antigen used for immunization is preferably selected from inactivated antigens, attenuated antigens, and subunit antigens.

The immunization of a hen against a selected antigen may be performed by inoculation with the antigen by any appropriate route such as subcutaneous, intraperitoneal, intramuscular, or intravenous injection, or oral administration. Preferably a suitable adjuvant is administered in conjunction with the antigen to enhance the immunization. An adjuvant useful for this purpose is a water-in-oil emulsion adjuvant such as complete Freund's adjuvant. It has been found that the use of a suitable adjuvant is highly effective to maintain a high antibody titer in the eggs of an immunized hen for a prolonged period, thereby making it possible to produce the desired antibody-containing substance efficiently. The dose of the antigen is determined depending on the type of the antigen and adjuvant and the administration route in such a manner that an immune status is induced in the hen without developing excessive toxicity of the antigen therein.

Usually within a few weeks after the inoculation (initial immunization), the hen becomes sensitive to the antigen, i.e., immunized against the antigen. A specific antibody against the antigen is produced within the body of the hen, and an egg laid by the hen contains the specific antibody. The presence and the titer level of the specific antibody against the antigen in the hen and in eggs of the hen can be confirmed by a number of methods known to those skilled in the art of immunological tests.

After the initial immunization of the hen against the antigen, one or more boosters at an appropriate dose level may be administered in order to maintain a high antibody titer in the hen. Again in each booster administration, a suitable adjuvant may be used in conjunction with the antigen. The interval between the initial immunization and the first booster administration and between individual booster administrations depends on the type of the antigen and is preferably at least two weeks.

After it is confirmed that an adequate titer of the desired specific antibody is present in an egg laid by the immunized hen, an egg laid by the hen is collected, and if necessary, stored until use. Conveniently, a plurality of eggs laid by one or more hens which have been immunized against the same antibody are collected and processed together to produce the desired substance which contains an antibody or a transfer factor-like component specific for the antigen.

From the collected egg or eggs, the yolk or albumen or the overall ovum of each egg is separated. Since most antibodies are contained in the yolk of an egg, the yolk is usually separated for use in the production of the desired substance. However, specific antibodies against some antigens are believed to be primarily present in the albumen of an egg, and if such an antigen is used in the immunization of the hen, the albumen of each egg will be used in the production method according to the present method. In some cases, both the yolk and albumen (overall ovum) of each egg may be used.

The separated yolk or albumen or both which contains an antibody against the inoculated antigen is then homogenized or agitated strongly to form an emulsion. If desired, water may be added to the homogenizer. In a preferred embodiment, the resulting emulsion is directly dried to form a powder by a conventional technique such as spray drying or lyophilizing which does not cause a significant loss of the activity of the antibody. The powder thus obtained contains the specific antibody, and can be used as an antibody-containing substance for oral administration according to the present invention. According to this embodiment, the desired specific antibody-containing substance can be produced without complicated procedures for isolation of the immunoglobulin fraction from the emulsion. Such isolation procedures have been generally employed in the prior art for the production of antibody-containing substances.

When the antigen used in immunization of the hen is a bacterium which causes intestinal infectious diseases such as colibacillosis in calves or piglets, the antibody-containing powder obtained from an egg, usually the yolk thereof, of the immunized hen in the above manner has an activity against the antigen and therefore it is effective in protection of calves or piglets from attack by the same bacterium used in the immunization. Thus, the powder can be used in the prevention or treatment of intestinal infectious diseases such as colibacillosis and scours by oral administration of the powder.

The specific antibody-containing substance is also useful as additives in foods for livestock and poultry, cosmetics, and medicines, and in the field of serodiagnosis.

In another embodiment of the present invention, the emulsion of the egg yolk, albumen, or both of immunized hen or hens is separated into a fraction having a molecular weight of at most 10,000 and the remaining fraction having a larger molecular weight by means of ultrafiltration. The former fraction having a molecular weight of at most 10,000 is used to recover a substance which contains a transfer factor-like component specific for the antigen, while the remaining fraction which contains immunoglobulins having a molecular weight on the order of about 150,000 or greater can be used to produce a specific antibody-containing substance following the above-mentioned procedure, i.e., direct drying of the fraction into powder.

The above separation by ultrafiltration may be carried out, for example, as follows. To an emulsion of egg yolk, albumen, or both which contain the specific antibody, 1N hydrochloric acid is added to lower the pH sufficiently to cause precipitation of some solids, e.g., to pH 4.5. After removal of the precipitates by high-speed centrifuge, the supernatant is neutralized with 1N NaOH. The acidification and neutralization are preferably carried out with mild stirring. In place of the acidification and subsequent neutralization, the fraction may be treated with an organic solvent such as chloroform. The supernatant is then passed through an ultrafilter having a pore size through which those molecules having a molecular weight of at most 10,000 can pass. This pore size is approximately 0.45 microns. The pore size of the ultrafilter may be varied as long as the ultrafiltration is effective to remove substantially all the immunoglobulins, viruses, mycoplasmas, and bacteria. The fraction passing through the ultrafilter is collected. The collected fraction, i.e., the filtrate contains a transfer factor-like component as an active ingredient which is specific for the antigen used in the immunization. The filtrate is free of any virus, mycoplasma, bacterium, or immunoglobulin. All these procedures are preferably carried out at temperatures which are at most slightly above room temperature, e.g., in the temperature range of from 0° to 25° C. The filtrate thus obtained can be used as a substance containing a transfer factor-like component in accordance with the present invention, and it may be stored as a solution, or dried to form a powder or granules by a conventional technique such as lyophilizing.

The thus obtained substance which contains a transfer factor-like component has prospective usefulness in the treatment and prevention of various infectious diseases, and as additives in food for livestock and poultry, cosmetics, and medicines. Since this substance is free of any antibody or immunoglobulin, it can be administered parenterally without the need for previous acquisition of resistance to antibodies against the antigen, and without a risk of causing serum diseases and anaphylactic shock. Therefore, it would be beneficial in the treatment and prevention of various infectious diseases including intestinal and other diseases, and it can be administered whenever such administration is required.

At the present time, the immunological functions of the transfer factor-like component contained in the above fraction having a molecular weight of at most 10,000 are not known. It is believed that this fraction contains, in addition to the transfer factor-like component, the food factor having a molecular weight of at most about 1200 described in the aforementioned U.S. Pat. No. 4,402,938. There is a possibility that a part of the transfer factor-like component is the same as the food factor described in that U.S. patent. Accordingly, it is assumed that the above fraction containing a specific transfer factor-like component is useful as a nutrition supplement as is the food factor of the above U.S. patent.

As mentioned above, the remaining fraction which could not pass through the ultrafilter contains immunoglobulins, and therefore it can be used to produce an antibody-containing powder by drying into a powder in a conventional manner If desired, the remaining fraction, or the yolk, albumen or both which contains the specific antibody may be subjected to a conventional fractionation or purification procedure prior to drying into powder. The specific antibody-containing substance may be recovered as an emulsion or solution itself without drying into powder, but it is convenient and preferable to recover it as a solid such as a powder or granules for ease of storage.

According to the method of the present invention, many animals can be readily used at once to immunize against the selected antigen, and many different antigens can be readily used simultaneously to produce their respective antibodies, because the animals used in immunization are hens. Therefore, a substance which contains a specific antibody or a specific transfer factor-like substance can be produced inexpensively and in large amounts in any season of the year. It is also possible to systematically produce a number of these substance which contain a wide variety of different specific antibodies at the same time. In a preferred embodiment of the production method of an antibody-containing substance, the yolk, albumen, or overall ovum of an egg of an immunized hen is simply dried to form a powder after homogenization to yield the desired product without fractionation such as ultrafiltration. This embodiment is particularly advantageous due to the very simple procedure involved therein. When an adjuvant is used in conjunction with the antigen in the immunization of a hen, an antibody against the antigen is formed in such a manner that a high antibody titer is maintained in eggs of the hen for a prolonged period, thereby making it possible to produce the desired substance extremely efficiently and inexpensively.

The antibody-containing substance according to the present invention can be used in the treatment or prevention of intestinal infectious diseases such as colibacillosis and diarrhea in livestock by oral administration of the substance when a bacterium causing such a disease is used as an antigen in the immunization of a hen. The administration to an animal can be performed at any time without the need for the animal to acquire resistance to ovular antibodies. When the antibody-containing substance is recovered directly from the yolk, albumen, or both of an egg without fractionation, it contains, in addition to the specific antibody against the antigen, a transfer factor-like component contained in a fraction thereof having a molecular weight of 10,000 or less. Thus, it is useful for nutrition supplements, or as an additive to food for animals, cosmetics and medicines.

The following examples are given to further illustrate the present invention. It should be understood that the present invention is not limited to the specific details set forth in the examples.

EXAMPLE I

This example illustrates the preparation of a specific antibody-containing egg yolk powder from eggs of immunized hens.

Figure 1:
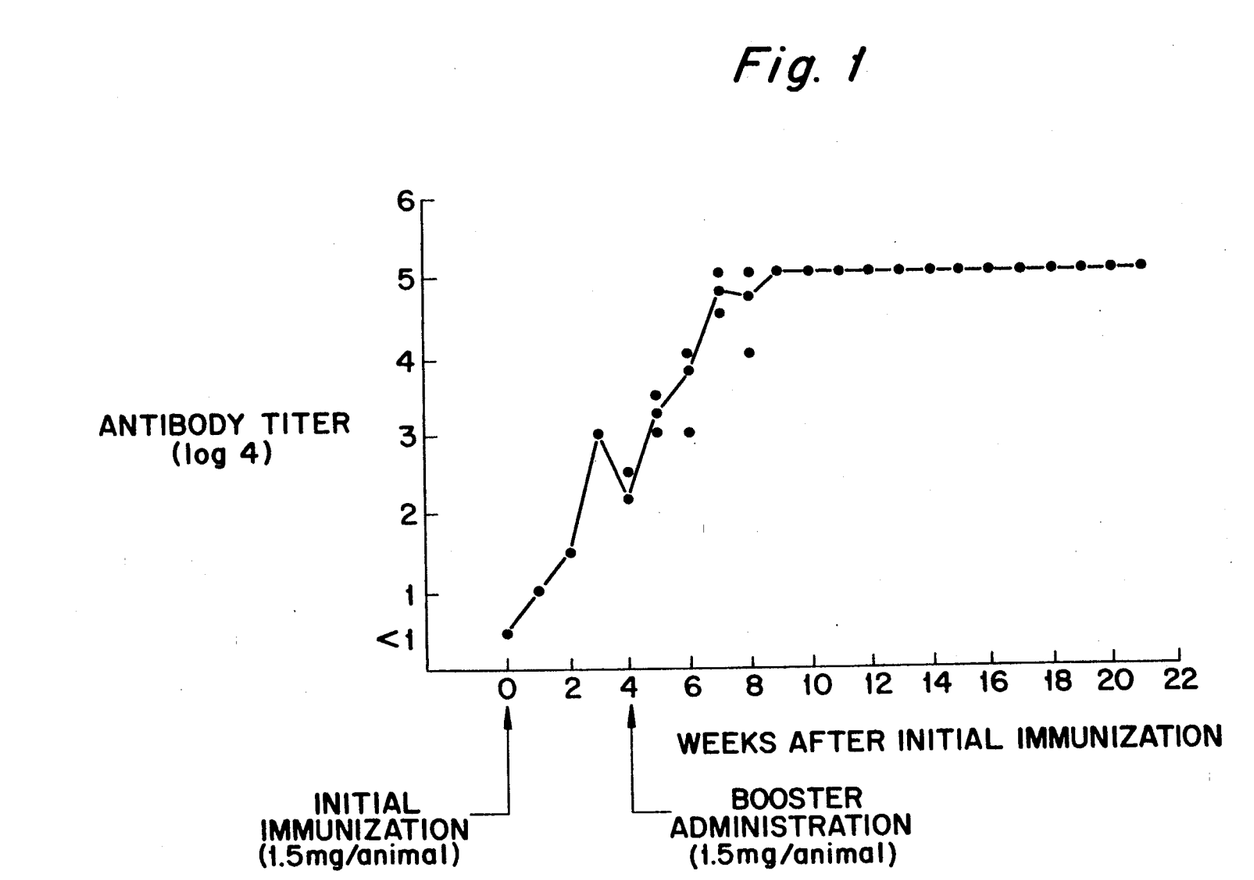
FIG. 1 is a graph showing weekly variation in the antibody titer in the egg yolk of a hen after immunization against 987P antigen from porcine enterotoxigenic *E. coli* (ETEC)

A 987P antigen which is a porcine ETEC (enterotoxigenic *E. coli*) known to cause diarrhea in pigs was injected intramuscularly into experimental mature hens at a dose of about 1.5 mg per animal to give the animals initial immunization against the antigen A water-in-oil emulsion type adjuvant which contained cells of dead tubercle bacillus was used in conjunction with the antigen. Four weeks after the initial immunization, the same antigen and adjuvant were injected in the same manner as a booster administration at a dose of about 1.5 mg per animal. Samples of the yolks of eggs laid by these hens were tested by an antibody assay method using an agglutination reaction with the antigen to ascertain the presence of a specific antibody against the antigen in the eggs. The antibody titer of each egg yolk sample was determined by a known method using the agglutination reaction The weekly variation in the antibody titer in the egg yolks of the immunized hens after the initial immunization is shown in FIG. 1. It can be seen from the graph of FIG. 1 that the antibody titer in the egg yolks reached a maximum value eight weeks after the initial immunization.

Using the same procedure as above but different antigens, pig K88 and K99, which are also coliform bacteria causing diarrhea in pigs, experimental mature hens were immunized against the selected antigen, and the presence of specific antibody against the antigen in the egg yolks of the hens and the antibody titer thereof were determined in the same manner Also in these experiments, the antibody titer reached a maximum value after a certain period.

After the antibody titer in the egg yolks reached a maximum value, the eggs laid by the immunized hens were collected in order to produce an antibody-containing egg yolk powder as follows.

The eggs laid by hens immunized against the same antigen were pooled and the yolks of these eggs were separated and combined together The combined yolks were then homogenized and the yolk homogenate was directly spray dried into a powder, which was recovered as an antibody-containing product The powder was stored at 37° C. in air.

The stability of the antibody-containing yolk powder stored at 37° C. was evaluated as follows. A one gram sample of the yolk powder before and after storage for various periods was dispersed in 9 ml of PBS (phosphate-buffered saline), and an equal volume of chloroform was added to the dispersion. After the mixture was vigorously shaken, it was centrifuged at 3000 rpm for 20 minutes. The supernatant was collected as the antibody-containing fraction, and the antibody titer of the supernatant was determined by an agglutination reaction with the antigen. The results are shown in Table 1 below.

As can be seen from Table 1, the antibody titer remained unchanged during storage for at least 6 months in all the powder products of different lots derived from various antigens.

The antibody-containing yolk powder thus obtained can be administered to animals by the oral route and is useful for the prevention and treatment of colibacillosis and diarrhea in animals, particularly pigs. It is also useful as an additive to food for animals.

TABLE 1

Antibody Titer Before and After Storage

| Lot. No. | Antigen | Storage Period at 37° C. (Month) | | | | |
|---|---|---|---|---|---|---|
| | | 0 | 1 | 2 | 3 | 6 |
| 1 | K88 | 128 | 128 | 128 | 128 | 128 |
| | K99 | 128 | 128 | 128 | 128 | 128 |
| | 987P | 256 | 256 | 256 | 256 | 256 |
| 2 | K88 | 256 | 256 | 256 | 256 | 256 |
| | K99 | 256 | 256 | 256 | 256 | 256 |
| | 987P | 512 | 512 | 512 | 512 | 512 |
| 3 | K88 | 512 | 512 | 512 | 512 | 512 |
| | K99 | 512 | 512 | 512 | 512 | 512 |
| | 987P | 512 | 512 | 512 | 512 | 512 |

EXAMPLE II

This example illustrates the preparation of a substance which contains a transfer factor-like component specific for the antigen used in immunization of a hen.

Mature hens were immunized against 987P+ETEC in the manner described in Example 1, and after the antibody titer of the egg yolk of the immunized hens reached a maximum value, eggs of the hens were collected. About 5 kg of the overall ova (yolk plus albumen) of these eggs which contained a specific antibody against the 987P antigen were stirred to form an egg emulsion The egg emulsion was diluted with an equal volume of PBS and stirred in a mixer for 15 minutes. To the dilute egg emulsion, 1N hydrochloric acid was added to adjust the pH of the emulsion to 4.5 and the emulsion was stirred for an additional 15 minutes The precipitated solids were removed by high-speed centrifuging. After the supernatant was neutralized with 1N NaOH solution, it was passed through an ultrafilter having a pore size of 0.45 microns so as to collect a fraction having a molecular weight of about 10,000 or less. The collected fraction contained a transfer factor-like component specific for the antigen used in the immunization (987P+ETEC)

EXAMPLE III

This example illustrates the therapeutic activity of the antibody-containing egg yolk powder obtained in Example 1 from the hens immunized against 987P antigen of porcine ETEC.

To each of newborn pigs weighing from 0.97 to 1.8 kg which had already taken colostrum, 1.5 g of the spray dried egg yolk powder obtained in Example 1 which contained a specific antibody against 987P+ETEC antigen and had an antibody titer of 1000 was administered as a solution in an artificial milk whenever the milk was fed to the animal three times a day. The administration of the egg yolk powder conducted in the above manner three times a day was continued to the end of the experiment in the animals of an administered group. From 21 to 23 hours after the birth, the newborn animal was challenged by the same 987P antigen as used in the immunization of the hens by oral administration of the antigen at a dose of $2 \times 10^{10}$ cells per animal Each of the newborn pigs of a control group was challenged by the above antigen in the same manner while they were fed on the same milk in which the above antibody-containing egg yolk powder was not dissolved.

Figure 2:
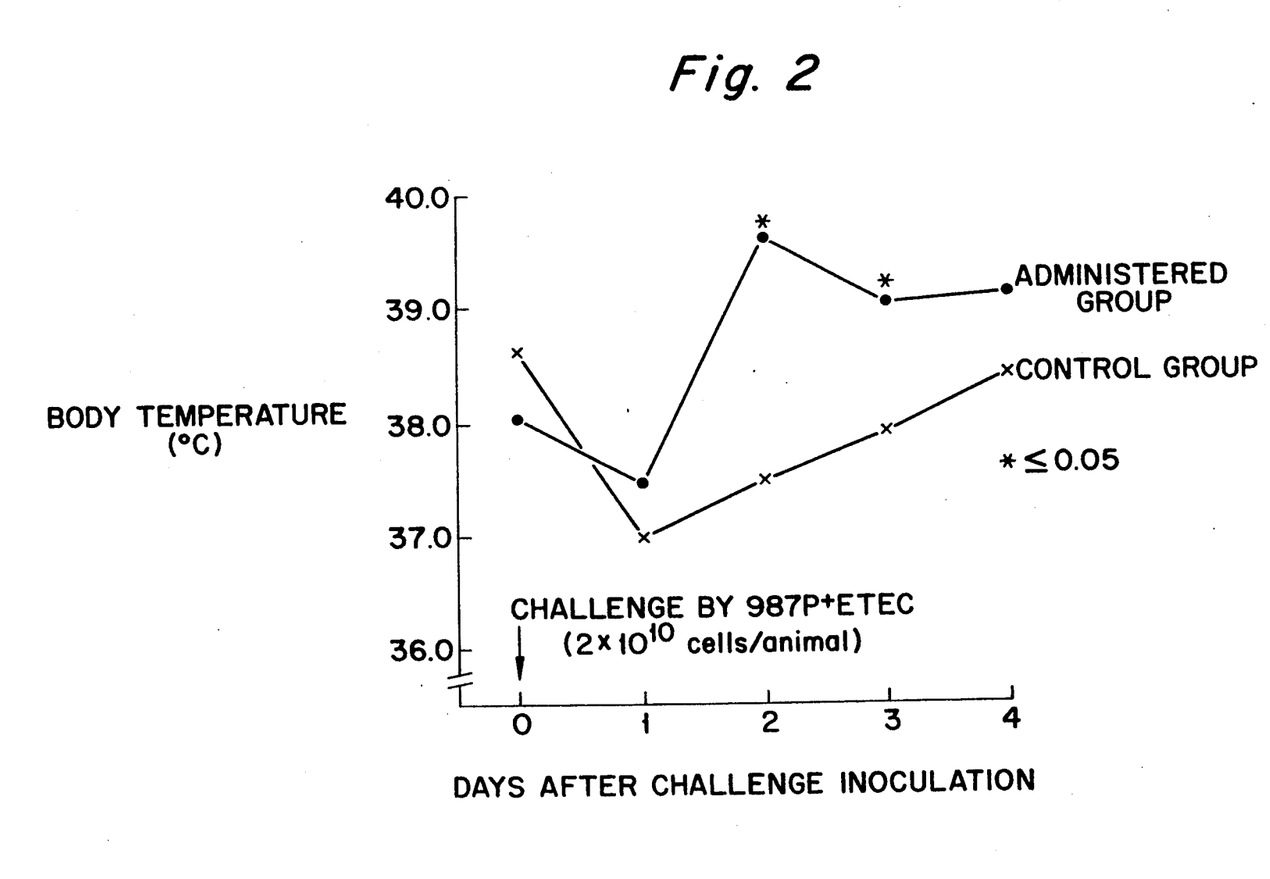
FIG. 2 is a graph showing variation in body temperature of newborn piglets after challenge by 987P+ETEC in which powder of the yolks recovered from eggs of hens immunized against the same antigen was orally administered to the animals in the administered group, while such administration is not employed in the control group.
Figure 3:
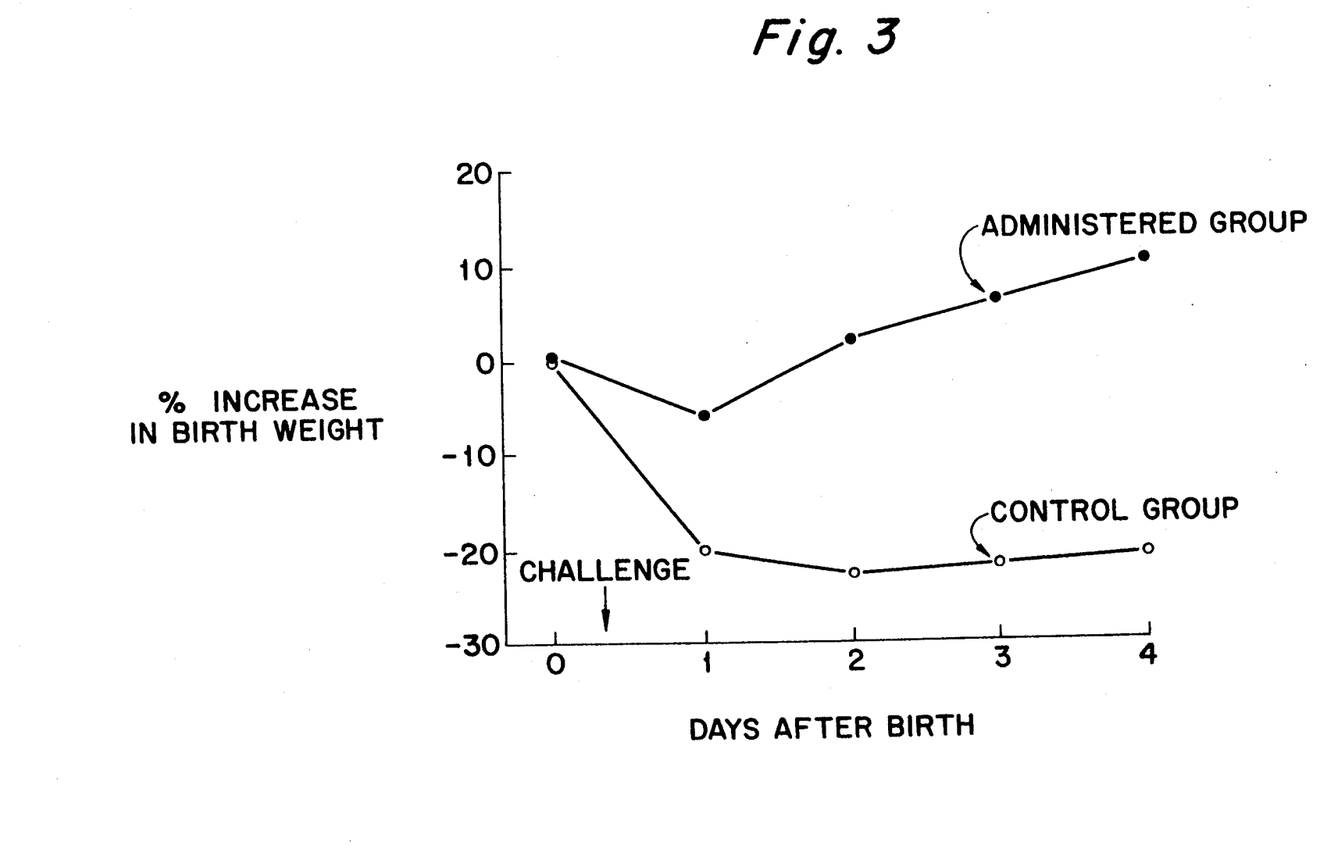
FIG. 3 is a graph showing the weight gain of newborn piglets after challenge inoculation with 987P+ETEC.

The body temperature variation, clinical manifestations, weight gain, and the isolation rate of the challenge organisms in each test animal were evaluated and the results are shown in FIGS 2 and 3, and Tables 2 to 4.

From FIG. 2, which shows the variation in body temperature of the test animals after challenge by the antigen, 987P+ETEC, it can be seen that the body temperature of the animals in the administered group initially decreased but was soon recovered to the original level (about 2 days after the challenge). On the contrary, the recovery of body temperature of the animals in the control group required a few days longer.

The clinical manifestations with respect to the fecal conditions after the challenge are shown in Table 2, from which it can be seen that the stools of all the animals in the administered group returned to normal three days after the challenge, while the stools of none of the animals in the control group returned to normal even after five days, and some animals in the control group died within 5 days of challenge.

The same tendency can be seen from the results of Tables 3 and 4 which show the isolation rate of challenge organisms from feces and small intestines. In all the animals of the administered group, the organisms were not isolated from the feces or small intestines. In contrast, in all the animals of the control group, the organisms grew in both the feces and the small intestines.

Referring to FIG. 3 which shows the weight gain of newborn pigs in the administered and control groups, 22 hours after the challenge, the weight gain of the pigs in the administered group transiently decreased, but attained to the normal level 2 days after the birth. In contrast, the weight gain of the control pigs rapidly decreased after the challenge, and the growth suppression due to the challenge persisted until 4 days after the birth.

Thus, it is apparent from the above results that the specific antibody-containing yolk powder according to the present invention has a therapeutic activity in the protection of an animal from challenge by the antigen used in the immunization of hens.

The activity of a substance which contains a specific antigen or specific transfer factor-like component in accordance with the present invention will be effective even in humans. Thus, such substance can be administered to animals including humans.

The present invention has been described with respect to preferred embodiments thereof. It should be understood, however, that various modifications can be made without departing from the concept of the invention, and such modifications are encompassed in the scope of the present invention.

What is claimed is:

1. A method for preventing or treating an intestinal infectious disease in a neonatal mammal caused by a pathogenic organism, said method comprising orally administering to a neonatal mammal, which has not acquired resistance to a specific antibody-containing substance, said specific antibody-containing substance being obtained rom he overall ovum, the yolk of the albumen of eggs laid by hens which have been immunized against a pathogenic organism as an antigen in an effective amount for preventing or treating an intestinal infectious disease caused by said pathogenic organism, said specific antibody-containing substance containing a specific antibody which is active against said antigen.

2. A method according to claim 1, wherein eh specific antibody-containing substance is obtained from the entire portion of the overall ovum, yolk or albumen of the egg without fractionation thereof.

3. A method according to claim 1, wherein the specific antibody-containing substance is obtained from a fraction of the overall ovum, yolk or albumen of the egg which contains the antibody.

TABLE 2

| Days After Challenge | Clinical Manifestations After Challenge by 987P+ ETEC | | | | | | | | | |
|---|---|---|---|---|---|---|---|---|---|---|
| | Administered Group | | | Control Group | | | | | | |
| | 1(♂) | 2(♀) | 3(♀) | 4(♂) | 5(♂) | 6(♂) | 7(♀) | 8(♂) | 9(♀) | 10(♂) |
| 0 | 0 | 0 | 0 | 0 | 0 | 0 | 0 | 0 | 0 | 0 |
| 1 | 2 | 2 | 2 | 3 | 3 | 3 | 3 | 3 | 3 | 3 |
| 2 | 1 | 1 | 1 | 3 | 3 | 3 | 4 | 3 | 3 | 3 |
| 3 | 0 | 0 | 0 | 3 | 4 | 3 | . | 2 | 3 | 3 |
| 4 | 0 | 0 | 0 | 3 | . | 3 | . | 2 | 3 | 3 |
| 5 | 0 | 0 | 0 | 2 | . | 2 | . | 2 | 2 | 2 |

Manifestations:
0 = Normal stool;
1 = Soft stool (with shape)
2 = Mild diarrhea (without shape)
3 = Severe watery diarrhea;
4 = Death

TABLE 3

| Days After Challenge | Isolation of the Challenge Organisms From Feces of Administered and Control Pigs | | | | | | | | | |
|---|---|---|---|---|---|---|---|---|---|---|
| | Administered Group | | | Control Group | | | | | | |
| | 1(♂) | 2(♀) | 3(♀) | 4(♂) | 5(♂) | 6(♂) | 7(♀) | 8(♂) | 9(♀) | 10(♂) |
| 0 | — | — | — | — | — | — | — | — | — | — |
| 1 | — | — | — | +++ | +++ | ++ | + | +++ | ++ | +++ |
| 2 | — | — | — | +++ | +++ | +++ | . | +++ | +++ | +++ |
| 3 | — | — | — | ++ | ++ | + | . | + | +++ | +++ |
| 4 | — | — | — | ++ | . | + | . | + | ++ | +++ |

Evaluation based on the proportion of colonies of the challenged bacteria on DHL agar plate.
+ = ca. 50%;
++ = ca. 80%;
+++ = ca. 100%

TABLE 4

| Portion | Isolation of Challenge Organisms From the Content of the Small Intestines of Administered and Control Pigs | | | | | | | | | |
|---|---|---|---|---|---|---|---|---|---|---|
| | Administered Group | | | Control Group | | | | | | |
| | 1(♂) | 2(♀) | 3(♀) | 4(♂) | 5(♂)* | 6(♂) | 7(♀)* | 8(♂) | 9(♀) | 10(♂) |
| Duodenum | — | — | — | — | — | ++ | + | ++ | +++ | +++ |
| Jejunum | — | — | — | — | — | — | +++ | ++ | +++ | +++ |
| Ileum | — | — | — | +++ | ++ | +++ | +++ | ++ | +++ | +++ |

Evaluation based on the proportions of colonies of the challenged bacteria on DHL agar plate.
+ = ca. 50%;
++ = ca. 80%;
+++ = ca. 100%
Sampling was carried out at death in Animals Nos. 5 and 7, or 5 days after the challenge in the other animals.

4. A method according to claim 1, wherein eh immunization of the hen is carried out by administration of the antigen in conjunction with a water-in-oil emulsion adjuvant.

5. A method according to claim 1, wherein eh specific antibody-containing substance is in the form of powder obtained by stirring the entire portion of the overall ovum, yolk or albumen of the egg into an emulsion and drying the emulsion to form a powder.

6. A method for preventing of treating a colibacillosis in a neonatal mammal caused by a coliform bacterium, said method comprising orally administering to a neonatal mammal, which has not acquired resistance to a specific antibody-containing substance, said specific antibody-containing substance being obtained from eh overall ovum, the yolk or the albumen of eggs laid by hens which have been immunized against a coliform bacterium as an antigen in an effective amount of preventing or treating a colibacillosis caused by said coliform bacterium, said specific antibody-containing substance containing a specific antibody which is active against said antigen.

7. A method for preventing or treating diarrhea in a neonatal mammal caused by an nterotoxigenic *E. coli*, said method comprising orally administering to a neonatal a mammal, which has not acquired resistance to a specific antibody-containing substance, said specific antibody-containing substance being obtained form he overall ovum, the yolk or the albumen of eggs laid by hens which have been immunized against an enterotoxigenci *E. coli* as an antigen in an effective amount for preventing or treating diarrhea caused by said enterotoxigenic *E. coli*, said specific antibody-containing substance containing a specific antibody which is active against said antigen.

* * * * *

US005080895B1

REEXAMINATION CERTIFICATE (3458th)

United States Patent [19]

Tokoro

[11] B1 5,080,895

[45] Certificate Issued Mar. 10, 1998

[54] SPECIFIC ANTIBODY-CONTAINING SUBSTANCE FROM EGGS AND METHOD OF PRODUCTION AND USE THEREOF

[75] Inventor: Hideo Tokoro, Tokyo, Japan

[73] Assignee: Ghen Corporation, Gifu, Japan

Reexamination Request:
No. 90/004,638, May 16, 1997

Reexamination Certificate for:
Patent No.: 5,080,895
Issued: Jan. 14, 1992
Appl. No.: 679,839
Filed: Apr. 1, 1991

Related U.S. Application Data

[63] Continuation of Ser. No. 338,417, Aug. 4, 1988, abandoned, which is a continuation of Ser. No. 933,187, Nov. 21, 1986, abandoned.

[30] Foreign Application Priority Data

Nov. 25, 1985 [JP] Japan ................................. 60-264108
Sep. 17, 1986 [JP] Japan ................................. 61-218859

[51] Int. Cl.$^6$ ................................................ A61K 39/395
[52] U.S. Cl. ............................... 424/157.1; 424/169.1; 530/367; 530/368; 530/389.5; 530/861
[58] Field of Search ....................... 424/157.1, 169.1; 530/367, 368, 389.5, 861

[56] References Cited

U.S. PATENT DOCUMENTS

| | | | |
|---|---|---|---|
| 3,984,539 | 10/1976 | Khouw et al. | 424/87 |
| 4,284,623 | 8/1981 | Beck | 424/85 |
| 4,340,591 | 7/1982 | Lucotte et al. | 424/177 |
| 4,357,272 | 11/1982 | Polson | 260/112 R |
| 4,402,938 | 9/1983 | Collins et al. | 424/85 |
| 4,534,971 | 8/1985 | Fisher | 514/21 |
| 4,550,019 | 10/1985 | Polson | 424/85 |
| 4,971,794 | 11/1990 | Linggood et al. | 424/92 |

FOREIGN PATENT DOCUMENTS

| | | |
|---|---|---|
| 0 152 270 | 8/1985 | European Pat. Off. |
| 59-73528 | 4/1984 | Japan |
| 2 057 451 | 4/1981 | United Kingdom |

OTHER PUBLICATIONS

Heller, E.D., Research in Veterinary Science, vol. 18, pp. 117–120 (1975).
Sherman et al., Infection and Immunity, Vo. 42, No. 2, pp. 653–658 (1983).
Bade et al., Journal of Immunological Methods, vol. 72, pp. 421–426 (1984).
Lösch et al., J. Vet. Med. B. vol. 33, pp. 609–619 (1986).
Ikemori et al., Veterinary Microbiology, (in press, 1997).
Sadowski et al., Basic Life Science, 25:93–99 (1983).
Burger et al., "Antibodies to Human Plasma Kallikrein From Egg Yolks of an Immunized Hen: Preparation and Characterization," Thrombosis Research, vol. 40, No. 2, pp. 283–288 (1985).

Carroll et al., "Antibodies to Calf Thymus RNA Polymerase II from Egg Yolks of Immunized Hens," Jnl. of Biol. Chem., vol. 258, No. 1, pp. 24–26, (Jan. 10, 1983).

Polson et al., "Isolation of Viral IgY Antibodies From Yolks of Immunized Hens," Immun. Comm., vol. 9, No. 5, pp. 475–493 (1980).

Polson et al., "Antibodies to Proteins From Yolk of Immunized Hens," Immun. Comm., vol. 9, No. 5, pp. 495–514 (1980).

Dunnick et al., "Lack of Antigen Fragments in Guinea Pig Transfer Factor–like Activity," Clinical Immunology and Imunopathology, vol. 17, pp. 55–65 (1980).

Bartz et al., "Prevention of Murine Rotavirus Infection with Chicken Egg Yolk Immunoglobulins," Jnl of Infectious Diseases, vol. 142, No. 3, pp. 439–441 (Sep. 1980).

Webster's New World/Stedman's Concise Medical Dictionary, p. 494 (1987).

Dunnick et al., "Lack of Antigen Fragments in Guinea Pig Transfer Factor–like Activity," Biol. Abstr., No. 2892, vol. 71, No. 1, p. 302 (Jan. 1, 1981).

Polson et al., "Antibodies to Proteins From Yolk of Immunized Hens," Chem. Abstr., No. 28708b, vol. 94, No. 5, p. 405 (Feb. 2, 1981).

Polson et al., "Isolation of Viral IgY Antibodies From Yolks of Immunized Hens," Chem. Abstr., No. 28656h, vol. 94, No. 5, p. 400 (Feb. 2, 1981).

Carroll et al., "Antibodies to Calf Thymus RNA Polymerase II from Egg Yolks of Immunized Hens," Chem. Abstr., No. 70128v, vol. 98, No. 9, p. 468 (Feb. 28, 1983).

Burger et al., "Antibodies to Human Plasma Kallikrein From Egg Yolks of an Immunized Hen: Preparation and Characterization," Chem. Abstr., No. 4457t, vol. 104, No. 1, p. 410 (Jan. 6, 1986).

*Primary Examiner*—Chhaya D. Sayala

[57] ABSTRACT

A substance which contains a specific antibody or specific transfer factor-like component is produced from the yolks or albumens or both of eggs of a hen which has been immunized against a selected antigen such as a pathogenic bacteria. The substance is active against the antigen, and is useful for protecting animals from attack by the same antigen as used in immunization of the hen. It is also useful as additives in food for animals, cosmetics, and medicines. The transfer factor-like component is recovered from a fraction of at most 10,000 in molecular weight of the yolks or albumens or both of the eggs.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-2, and 4-7 are determined to be patentable as amended.

Claim 3, dependent on an amended claim, is determined to be patentable.

New claims 8-11 are added and determined to be patentable.

1. A method for preventing or treating an intestinal infectious disease in a neonatal [mammal] *piglet or calf* caused by a pathogenic organism, said method comprising orally administering to a neonatal [mammal] *piglet or calf*, which has not acquired resistance to a specific antibody-containing substance, said specific antibody-containing substance being obtained [rom he] *from the* overall ovum, the yolk [of] *or* the albumen of eggs laid by hens which have been immunized against [a] *said* pathogenic organism as an antigen in an effective amount for preventing or treating an intestinal infectious disease caused by said pathogenic organism, said specific antibody-containing substance containing a specific antibody which is active against said antigen.

2. A method according to claim 1, wherein [eh] *the* specific antibody-containing substance is obtained from the entire portion of the overall ovum, yolk or albumen of the egg without fractionation thereof.

4. A method according to claim 1, wherein [eh] *the* immunization of the hen is carried out by administration of the antigen in conjunction with a water-in-oil emulsion adjuvant.

5. A method according to claim 1, wherein [eh] *the* specific antibody-containing substance is in the form of powder obtained by stirring the entire portion of the overall ovum, yolk or albumen of the egg into an emulsion and drying the emulsion to form a powder.

6. A method for preventing [of] *or* treating [a] colibacillosis in a neonatal mammal caused by a coliform bacterium, said method comprising orally administering to a neonatal mammal, which has not acquired resistance to a specific antibody-containing substance, said specific antibody-containing substance being obtained from [eh] *the* overall ovum, the yolk or the albumen of eggs laid by hens which have been immunized against [a] *said* coliform bacterium as an antigen in an effective amount [of] *for* preventing or treating [a] colibacillosis caused by said coliform bacterium, said specific antibody-containing substance containing a specific antibody which is active against said antigen.

7. A method for preventing or treating diarrhea in a neonatal mammal caused by an [nterotoxigenic] *enterotoxigenic* E. coli, said method comprising orally administering to a neonatal [a] mammal, which has not acquired resistance to a specific antibody-containing substance, said specific antibody-containing substance being obtained [form he] *from the* overall ovum, the yolk or the albumen of eggs laid by hens which have been immunized against [an enterotoxigenci] *said enterotoxigenic* E. coli as an antigen in an effective amount for preventing or treating diarrhea caused by said enterotoxigenic E. coli, said specific antibody-containing substance containing a specific antibody which is active against said antigen.

*8. A method according to claim 6, wherein said neonatal mammal is a neonatal piglet or calf.*

*9. A method according to claim 7, wherein said neonatal mammal is a neonatal piglet or calf.*

*10. A method for preventing or treating an intestinal infectious disease in a neonatal mammal caused by a pathogenic organism, said method comprising orally administering to a neonatal mammal, which has not acquired resistance to a specific antibody-containing substance, said specific antibody-containing substance being obtained from the overall ovum, the yolk or the albumen of eggs laid by hens which have been immunized against said pathogenic organism as an antigen in an effective amount for preventing or treating an intestinal infectious disease caused by said pathogenic organism, said specific antibody-containing substance containing a specific antibody which is active against said antigen and wherein the specific antibody-containing substance is in the form of powder obtained by stirring the entire portion of the overall ovum, yolk, or albumen of the egg into an emulsion and drying the emulsion to form a powder.*

*11. A method according to claim 10, wherein said neonatal mammal is a neonatal piglet or calf.*

* * * * *